US012758787B2

(12) United States Patent
Moravec

(10) Patent No.: US 12,758,787 B2
(45) Date of Patent: Oct. 13, 2026

(54) MONOPHASIC MAGNETIC STIMULATOR FOR TRANSCRANIAL MAGNETIC STIMULATION

(71) Applicant: DEYMED DIAGNOSTIC S.R.O., Hronov (CZ)

(72) Inventor: Miroslav Moravec, Hronov (CZ)

(73) Assignee: DEYMED DIAGNOSTIC S.R.O., Hronov (CZ)

( * ) Notice: Subject to any disclaimer, the term of this patent is extended or adjusted under 35 U.S.C. 154(b) by 481 days.

(21) Appl. No.: 18/577,320

(22) PCT Filed: Jul. 8, 2022

(86) PCT No.: PCT/CZ2022/000031
§ 371 (c)(1),
(2) Date: Jan. 8, 2024

(87) PCT Pub. No.: WO2023/280332
PCT Pub. Date: Jan. 12, 2023

(65) Prior Publication Data

US 2024/0359027 A1 Oct. 31, 2024

(30) Foreign Application Priority Data

Jul. 9, 2021 (CZ) .............................. CZ 2021-333
Jul. 4, 2022 (CZ) .............................. CZ 2022-299

(51) Int. Cl.
*A61N 2/00* (2006.01)
*A61N 2/02* (2006.01)

(52) U.S. Cl.
CPC ............... *A61N 2/006* (2013.01); *A61N 2/02* (2013.01)

(58) Field of Classification Search
CPC . A61N 2/006; A61N 2/00; A61N 2/02; A61N 2/008; A61N 1/40; A61N 1/00; A61N 1/05
(Continued)

(56) References Cited

U.S. PATENT DOCUMENTS 5,047,005 A 9/1991 Cadwell
11,247,065 B2 * 2/2022 Katznelson ............ A61N 2/006
(Continued)

FOREIGN PATENT DOCUMENTS

DE 10 2012 101921 A1 10/2013
EP 2 907 540 A1 8/2015

OTHER PUBLICATIONS

International Search Report / Written Opinion for the International Search Authority for corresponding PCT/CZ2022/000031, mailed Oct. 13, 2022.

(Continued)

*Primary Examiner* — Hai L Nguyen
(74) *Attorney, Agent, or Firm* — Notaro, Michalos & Zaccaria P.C.

(57) ABSTRACT

A circuit wiring arrangement of a monophasic stimulator for transcranial magnetic stimulation is described. A stimulation capacitor is connected via a switch and a limiting medium to a source of a stimulation energy while the stimulation capacitor is connected in parallel with a diode and with a braking resistor. The braking resistor is connected in series with the diode. A stimulation coil is further connected in parallel to the stimulation capacitor via a switching thyristor. A braking capacitor is also connected in series with the diode. A discharging resistor is connected in parallel to the braking capacitor. The discharging resistor is connected in series with the diode.

6 Claims, 8 Drawing Sheets

(58) Field of Classification Search
USPC .... 327/100, 102, 103, 108, 110; 600/13, 14, 600/15
See application file for complete search history.

(56) References Cited

U.S. PATENT DOCUMENTS

| | | | | |
|---|---|---|---|---|
| 11,666,774 | B2 * | 6/2023 | Weyh | A61N 1/40 607/2 |
| 12,564,726 | B1 * | 3/2026 | Schwarz | A61N 2/006 |
| 2008/0306326 | A1 | 12/2008 | Epstein | |
| 2009/0018384 | A1 | 1/2009 | Boyden et al. | |
| 2012/0108883 | A1 | 5/2012 | Peterchev | |
| 2018/0361168 | A1 | 12/2018 | Goetz | |
| 2020/0030622 | A1 | 1/2020 | Weyh et al. | |

OTHER PUBLICATIONS

International Application Status Report for corresponding PCT/CZ2022/000031 dated Dec. 21, 2023.

* cited by examiner

MONOPHASIC MAGNETIC STIMULATOR FOR TRANSCRANIAL MAGNETIC STIMULATION

FIELD OF INVENTION

The invention relates to a circuit wiring of a monophasic magnetic stimulator for transcranial magnetic stimulation specialized for measuring evoked potentials during cortex stimulation (TMS-EEG).

STATE OF THE ART in electrophysiology, all responses of the nervous system caused by irritation of the relevant receptor, nerve fiber, spinal cord or cerebral cortex are considered to be evoked potentials. The response of the nervous system during magnetic stimulation creates an electric voltage, or rather an electric current, which was created by electromagnetic induction under an influence of a rapidly changing magnetic field reaching such an intensity that it is able to cause neuron depolarization. Currently, for studies of evoked potentials generated by transcranial magnetic stimulation, so-called TEP or TMS evoked EEG, a monophasic impulse is most often used, which, unlike a biphasic impulse, causes depolarization of neurons morphologically oriented in only one direction, which is advantageous for the purposes of studying their the answer. For the purposes of this application, a monophasic pulse means a unipolar pulse with a steep onset and slow decay of the stimulation current, where at its end the magnitude and change of the current passing through the stimulation coil asymptotically decreases to zero. This impulse is created by a monophasic magnetic stimulator and its course can basically be divided into two parts. The first part of the monophasic pulse is the phase of active stimulation, i.e. the phase in which the monophasic magnetic stimulator creates its own impulse used in transcranial magnetic stimulation. The second part of the monophasic impulse is the relaxation phase, during which the impulse is coming to its end, i.e. runs down. While both parts of the monophasic pulse, or its phase, have an effect on the interference of the measured signal, ideally only the stimulation phase should have an effect on the stimulation. In practice, however, stimulation is partly negatively affected by the relaxation phase, in which the change in current through the stimulation coil over time still reaches quite high values. With existing solutions of monophasic magnetic stimulators, the relaxation phase takes a very long time, in practice it is a duration in the order of milliseconds, which limits the possibility of registering an undisturbed electrophysiological signal in the immediate vicinity of the stimulation coil just after stimulation.

Currently, the following types of magnetic stimulators are basically used for transcranial magnetic stimulation with a monophasic form of stimulation current:

A) A simple magnetic stimulator with passive braking of the stimulation current by means of a braking resistor, which is connected in series with diode D. In this magnetic stimulator, magnetic stimulation ends only at very low values of the current in the stimulation coil by spontaneous turning on of diode D, when at the same time due to polarity reversal the voltage on the stimulation capacitor C1 will also reverse the polarity of the thyristor and the stimulation circuit is disconnected. This termination process of monophasic magnetic stimulation therefore shows a rather long decay time of the stimulation impulse. It is true that they are relatively cheap, common and often used magnetic stimulators, but with this type of magnetic stimulator, it takes a very long time to slow down, i.a. brake, the magnetic stimulation, practically a few milliseconds. After this time, the exponentially decaying stimulation current no longer affects the stimulation, but it is still capable of interfering with the measured signal sensed near the stimulation site.

B) Magnetic stimulator allowing to set the width of the stimulation and relaxation phases, actively using external control of IGBT transistors or IGCT thyristors, which switch-off the active stimulation circuit at the required time. Both IGBT transistors and IGCT thyristors are switched in a very similar way to standard thyristors, but unlike these standard thyristors, they allow be turned off, i.e. interruption of the electric current passing through them, using external control at any time. In principle, this switch-off must be relatively fast, on the order of fractions to units of μs (microseconds), as long-term disconnection would result in significant energy losses and power overloading of the switching element. When switching off high electric currents, high voltage peaks occur due to parasitic inductances, which are hard to eliminate. To suppress these voltage peaks, which could cause a voltage breakdown of the power switching element, snubbers are almost always provided. The disadvantage of magnetic stimulators with IGBT transistors or IGCT thyristors is the very high price of these elements, which is many times higher than conventional thyristors that are turned off spontaneously due to the decrease in the magnitude of the passing current below the holding limit. Otherwise, magnetic stimulators with IBGT transistors typically use two voltage sources, positive and negative. The positive voltage source to start and the negative one to brake the stimulation coil.

Although this type of magnetic stimulator can suppress unwanted artifacts immediately after stimulation, in order to achieve the same high maximum intensities of the current passing through the stimulation coil as a simple magnetic stimulator of the A-type, they are several times, up to eight times more expensive.

FIG. 1 shows a wiring diagram of the first type, i.e. A-type, of monophasic magnetic stimulator, ensuring the creation of the necessary impulse during such a measurement. There is also a monophasic magnetic stimulator with a different wiring, where a diode D and a braking resistor R are connected in parallel with the stimulation coil L, but this does not change the course of the impulse. The disadvantage of monophasic magnetic stimulators—of the A-type is the long time of the relaxation phase/part of the monophasic pulse, which is not decisive for the stimulation parameters. Nevertheless, when co-registering the electrophysiological signal, under the above conditions, it can cause the formation of unwanted artifacts, which negatively affect the measurement results in the mentioned studies.

Subject of Invention

The above mentioned shortcomings are eliminated by a circuit wiring of a monophasic magnetic stimulator according to the invention. According to the present invention, an arrangement of a monophasic magnetic stimulator for transcranial magnetic stimulation is presented, which includes a stimulation capacitor connected via a switch and limiting means to a voltage source of a stimulation energy, a stimulation coil is connected in parallel to the stimulation capacitor, and this stimulation coil is connected to said stimulation capacitor via a switching thyristor, a diode is further connected in parallel to the stimulation capacitor, preferably in series combination with a brake resistor, while it is essential that a brake capacitor is connected in series with the diode and that in parallel to this brake capacitor a discharging resistor adapted to discharge this braking capacitor is connected. The arrangement of a monophasic magnetic stimulator refers to its wiring, and these two terms may be used interchangeably in the description. The main idea of the monophasic magnetic stimulator according to the invention is to ensure the end of the relaxation phase in a shorter time without a need to use active switching elements, thanks to the inclusion of a braking capacitor designed to achieve a braking effect at the end of the relaxation phase, when the current passing through the stimulation coil is already small. The braking resistor used in the current state of the art is not able to ensure this, as the voltage on it and thus its braking efficiency decreases linearly with decreasing current passing through the braking resistor.

Description of the function of the monophasic magnetic stimulator according to the invention:

At the beginning of the stimulation phase, the thyristor T turns on and the current passing through the stimulation coil from the stimulation capacitor begins to increase. A shape of the current through the stimulation coil L in time can be described by a sine function in the first quadrant with the duration of a quarter period determined by the oscillation of the LC circuit formed by the stimulation coil L and the stimulation capacitor C1. The typical duration of the stimulation phase in monophasic transcranial magnetic stimulation is 100 μs. During the transition from the stimulation phase to the relaxation phase, due to the transition of voltage C1 from positive to negative values, the diode D turns on. At the transition from the stimulation phase to the relaxation phase, the stimulation current reaches also its maximum values. However, the voltage on the stimulation coil and also the induced voltage in the stimulated biological tissue is almost zero at this time, because the current passing through the stimulation coil changes very slowly during this time, as it reaches a flat maximum. At the beginning of the relaxation phase, the braking capacitor C2 is fully discharged and it is gradually charged, which causes, together with the voltage on the braking resistor R1, essentially braking the current passing through the stimulation coil. At the beginning of the relaxation phase, the braking resistor R1 has a predominant effect on reducing the current passing through the stimulation coil, but towards the end, due to its charging, the influence of the braking capacitor C2 prevails, on which the voltage increases due to the passing current and thus its braking effect increases. At the end of the relaxation phase, due to the effect of the braking effect of the braking capacitor C2 the current passing through the stimulation coil will cease, which simultaneously turns off the diode D and switches-off the thyristor T. Subsequently, the braking capacitor C2 will be discharged by the discharging resistor R2, but this event is due to the duration of the stimulation and the relaxation phase is very slow because it lasts for hundreds of milliseconds. Thanks to this, the value of the discharging resistor R2 has a completely negligible effect on the stimulation parameters. Current and voltage courses on the described elements are shown in FIG. 8, FIG. 9 and FIG. 10.

A limiting device is also included in the magnetic stimulator to prevent a short circuit when charging the stimulation capacitor, which is directly connected to the source at this stage. The limiting device can be, for example, a resistor with an appropriate resistance or it can be another device that prevents a short circuit. For example, according to one advantageous embodiment of a monophasic magnetic stimulator, the limiting device can be arranged directly in the power source. In a particularly advantageous embodiment of the invention the limiting device is represented by a switching source, which prevents the occurrence of a short circuit already by its design, when charging the stimulation capacitor. The diode is connected in such a way that when charging the stimulation capacitor it prevents the current from passing through the braking resistor and, conversely, after transitioning to the relaxation phase, it allows the current to pass through the braking resistor and create a second-order damped oscillation circuit provided by the braking resistor R1, the stimulation coil L, the braking capacitor C2 and the stimulation capacitor C1. In order to understand all the phenomena in the circuitry according to the invention, it is appropriate to state that the stimulation voltage used to create a magnetic pulse by the stimulation coil is very high, a voltage in the order of kV units (kilovolts) is used. The stimulation capacitor usually has a capacity in the order of hundreds of μF (microfarads), but it must be able to hold an electric charge of the above-mentioned stimulation voltage, which makes it a very large and relatively expensive component. The braking capacitor has a capacity enabling the fast closing of the diode in the relaxation phase. i.e. corresponding to at least the capacity of the stimulation capacitor as will be described below, especially preferably the capacity of the braking capacitor exceeds the capacity of the stimulation capacitor by at least 4 times, but even more times, as will be described again below. Thanks to the braking capacitor, the diode D and the thyristor T will be turned off spontaneously, passively without the need for external intervention, essentially by reversing the voltage on the anode and cathode of the diode D, respectively the thyristor T into a closing direction.

Since the braking capacitor is only charged in the relaxation phase, it charges to a much lower voltage than the stimulation capacitor, as a result of which it can be rated at a significantly lower voltage than the voltage of the stimulation capacitor C1, and due to the lower absorbed energy, its dimensions are not as large as this is the case with the stimulation capacitor C1 and is therefore significantly cheaper, so it does not significantly increase the overall production cost of the monophasic magnetic stimulator.

The ratio of the amplitude of the voltage induced in the biological tissue during the relaxation phase and the amplitude of the voltage induced in the biological tissue during the stimulation phase is given by a relation $$U_{RELAX}/U_{STEM}=1/(N+1),$$

where N is a ratio of the electrical capacity of the braking capacitor C2 to the electrical capacity of the stimulating capacitor C1. Therefore, at least the size of the capacity of the stimulation capacitor C1 is considered as the lower limit of the applicability of the braking capacitor C2, due to the fact that the ratio of the amplitudes of the induced voltage of the relaxation and stimulation phases is at most 0.5. The half ratio of the amplitudes of the induced electric voltage in the biological tissue during the relaxation and stimulation phase is generally considered to be the limit value at which it is possible to speak of monophasic stimulation during magnetic stimulation. Just to illustrate, with biphasic stimulation, the voltage ratio of the stimulation and relaxation phase is approximately 1:1. The value of the ratio of the amplitude of the induced voltage of the relaxation phase to the amplitude of the induced voltage of the stimulation phase is generally considered to be 0.2 or even lower as the ideal shape of the course of the induced voltage of monophasic stimulation.

However, with monophasic stimulation with a ratio of both mentioned induced voltage amplitudes lower than 0.2, the electrophysiological response is no longer affected and therefore such a ratio is not used in clinical studies. For the above reasons, the most advantageous value of the electrical capacity of the braking capacitor C2 is at least four times the value of the stimulation capacitor C1.

Furthermore, if choosing the capacity of the braking capacitor C2 more than about 20 times the capacity of C1, the duration of the impulse would be prolonged without a positive effect on the magnetic stimulation. Such capacity would only result in an extension of the time during which it is not possible to register a useful electrophysiological signal due to the presence of the magnetic pulse. Particularly advantageously, the size of the capacity of the braking capacitor C2 ranges from four times to ten times the value of the capacity of the stimulation capacitor C1.

The main purpose of the braking resistor R1 is to dissipate a significant part of the energy contained in the stimulation coil and thereby to reduce demands on a voltage resistance of the braking capacitor C2, causing it is then unable to charge to such a high voltage in the relaxation phase as if the resistor R1 was omitted. Omission in this case means short-circuiting. Its value is chosen approximately in the same range as the value of the braking resistor for a monophasic magnetic stimulator according to the current state of the art, due to the equivalence of the course of the initial course of the stimulation current in the relaxation phase passing through the stimulation coil.

The main task of the discharging resistor R2 is to discharge the capacitor C2 to zero value and thereby enable its braking function during the next stimulation pulse. The resistance value of the discharging resistor R2 has almost no effect on the stimulation parameters, i.e. the course of the current through the stimulation coil, and its value should be chosen in such a way as to ensure the discharge of C2 until the moment of the next stimulation, which usually comes within a few seconds, first to about 0.5 seconds.

Further this invention uses an idea that when the braking capacitor C2 is connected in series with the diode D, preferably also with the braking resistor R1, the oscillation of the stimulation current in the stimulation circuit, which at the beginning of the stimulation is described by the transient process of the first order, is transformed into a current oscillation of the second order with a finite duration described by the transition event. The magnitude of the braking capacitor capacitance together with the braking resistor R1, if present, and with the inductance L will form a 2nd order resonant circuit. This means that the damping factor of the series RLC circuit formed by the stimulation coil L, the breaking resistor R1 and the stimulation capacitor C1 as well as the breaking capacitor C2, is less than one. Thanks to this technical solution, it is possible to use standard thyristors that switch off automatically when the current drops below the holding limit, i.e. not actively. For the purposes of this invention, the braking resistor R1 is also considered to be another suitable resistance-exhibiting element capable of fulfilling the same purpose.

Artifacts in a circuit wiring according to the invention arise in the same way, but have a shorter duration, which is important for the possibility of analyzing the electrophysiological response to the stimulus.

BRIEF DESCRIPTION OF DRAWINGS

Possible embodiments of the monophasic magnetic stimulator arrangement according to the invention will be more clearly understood from the following examples of embodiment of the monophasic magnetic stimulator with attached figures in which these implementations are depicted, where.

EXAMPLES OF EMBODIMENT

The implementation examples describe particularly advantageous variants of the arrangement of the monophasic magnetic stimulator according to the present invention. However, it is clear to the expert that other connection variants are also possible, in particular a combination of some of the mentioned connection elements is possible without departing from the inventive idea. The scope of protection should therefore not be understood as limited to the examples of implementation described here, but only within the scope of the interpretation of the content of the patent claims.

Figure 1:
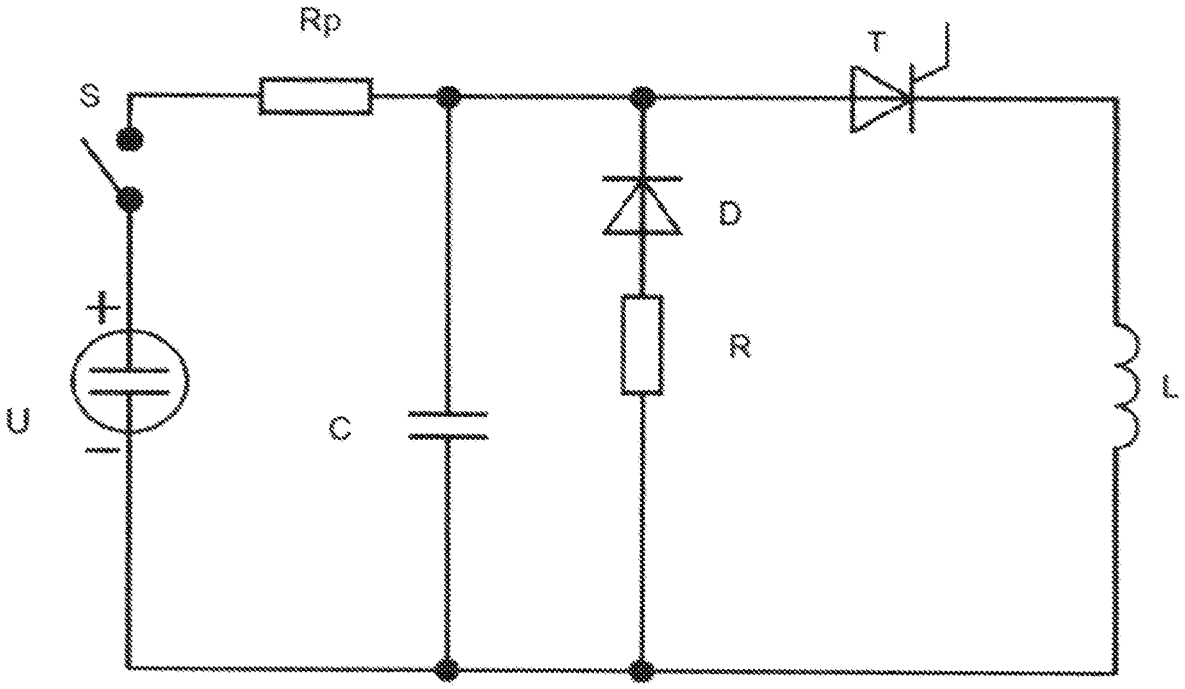
FIG. 1 represents a diagram of the arrangement of a monophasic stimulator according to the state of the art.

As already mentioned, FIG. 1 is a diagram of the arrangement of a monophasic magnetic stimulator according to the state of the art.

Figure 2:
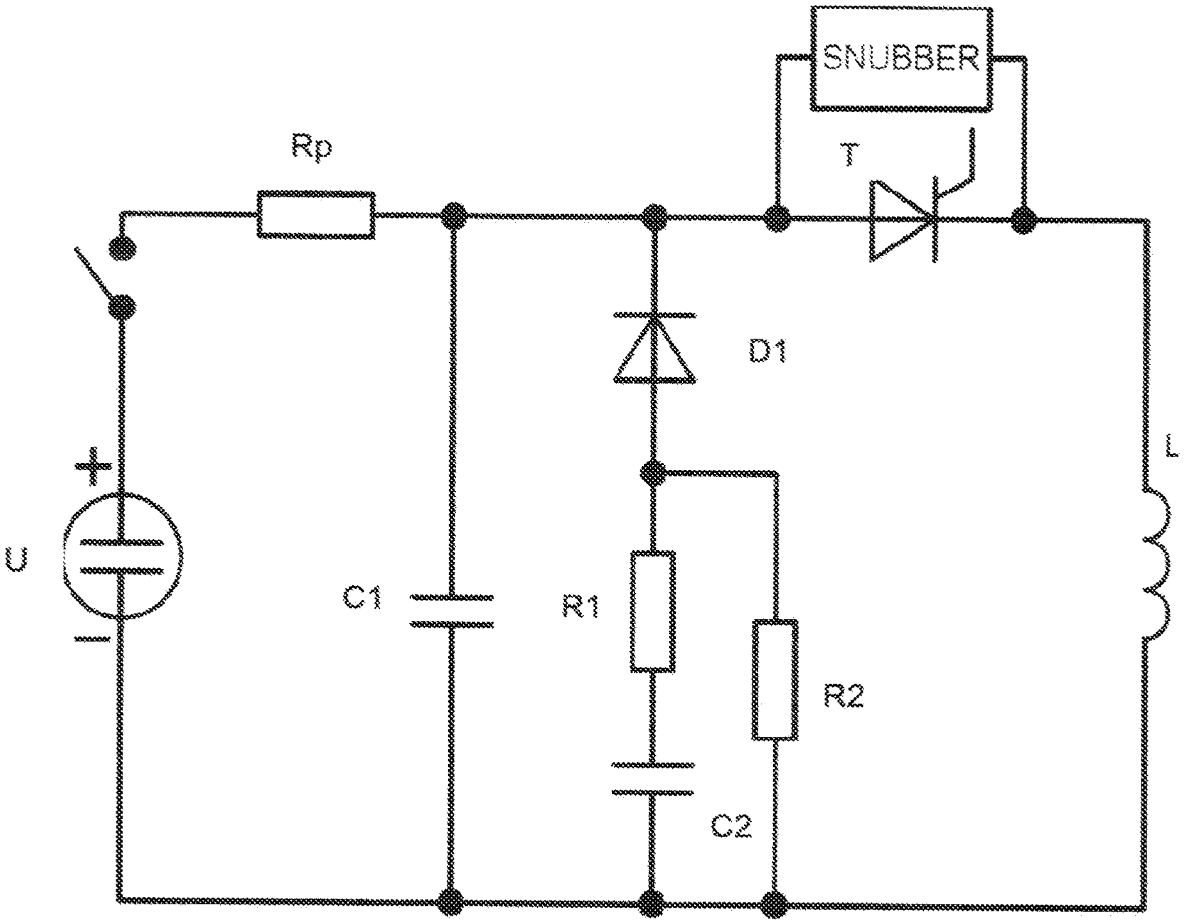
FIG. 2 represents the first embodiment of the arrangement of the monophasic magnetic stimulator for transcranial magnetic stimulation according to the invention.
Figure 3:
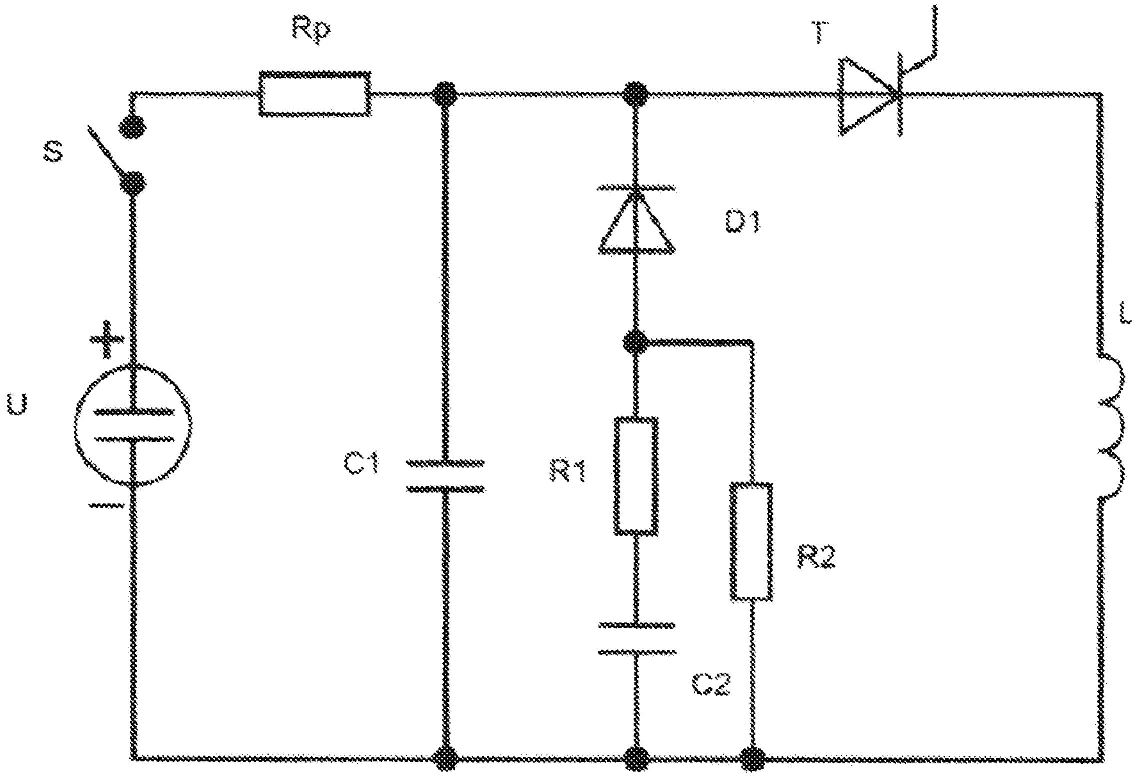
FIG. 3 represents the second embodiment of the arrangement of the monophasic magnetic stimulator for transcranial magnetic stimulation according to the invention, FIG. 4. represents the third embodiment of the arrangement of the monophasic magnetic stimulator for transcranial magnetic stimulation according to the invention.
Figure 4:
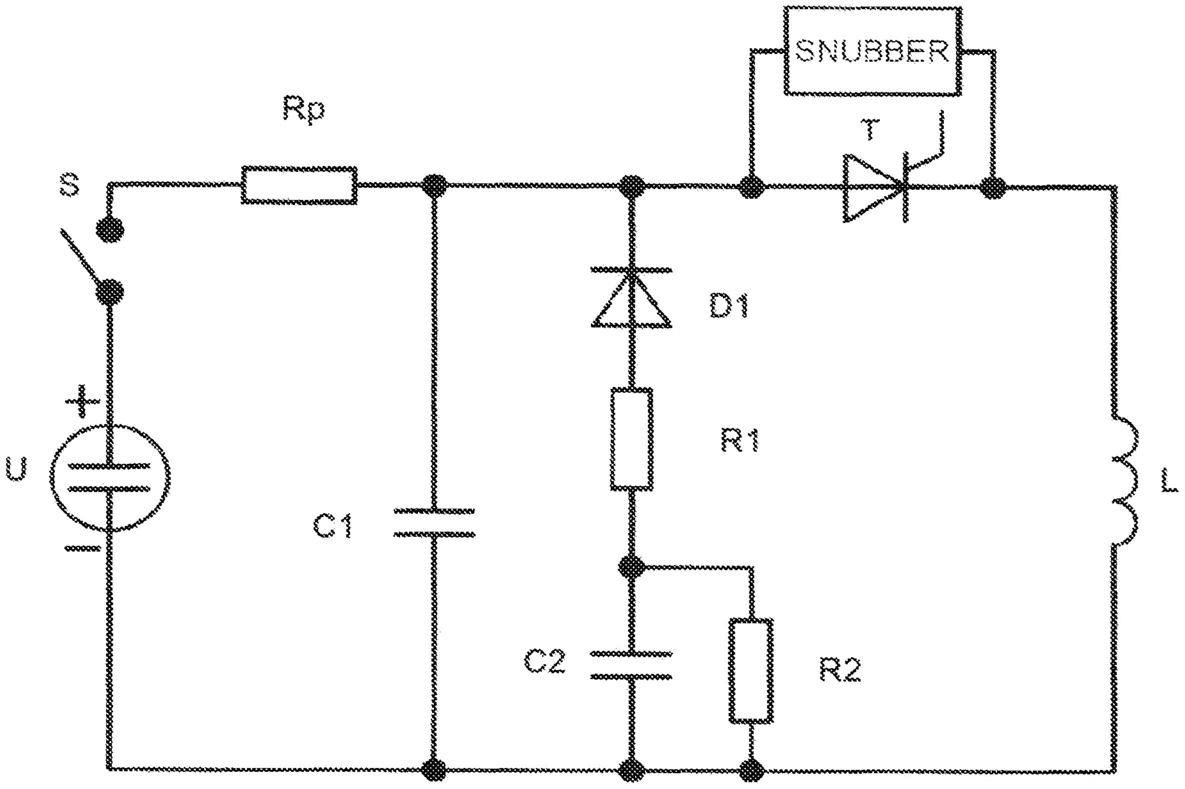
Figure 5:
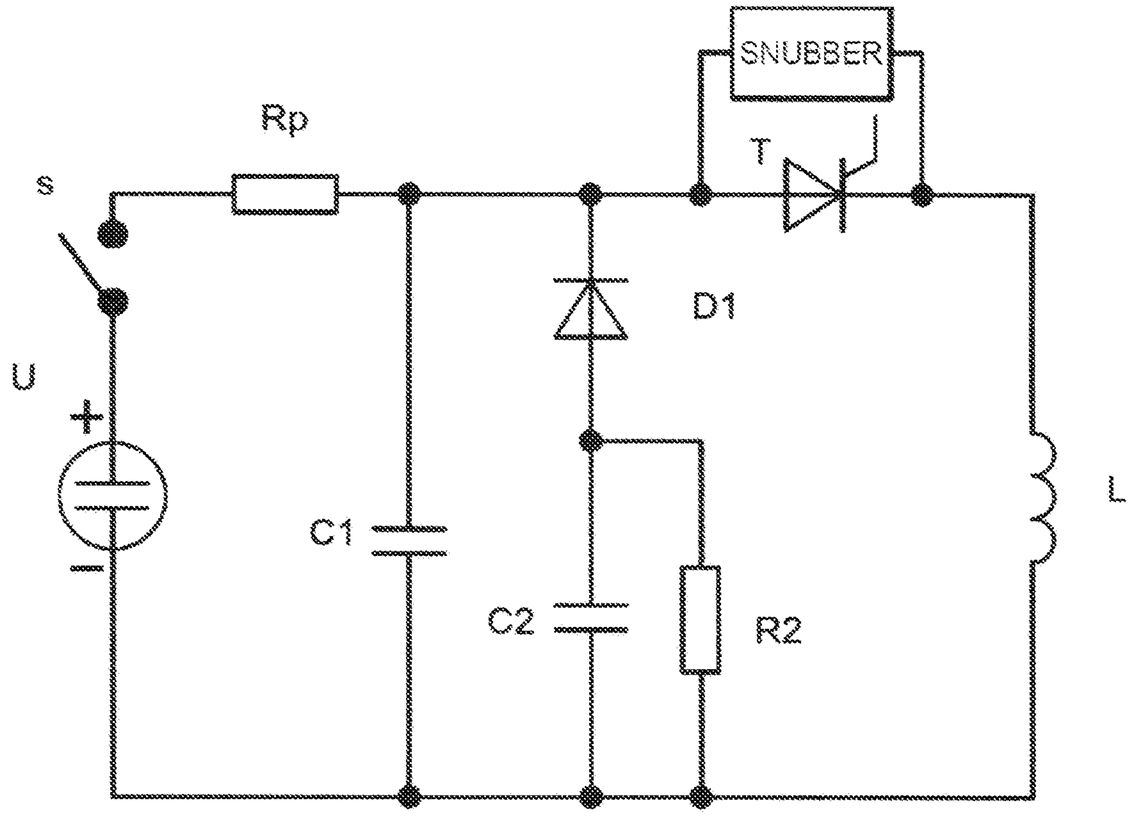
FIG. 5 represents the fourth embodiment of the arrangement of the monophasic magnetic stimulator for transcranial magnetic stimulation according to the invention.
Figure 6:
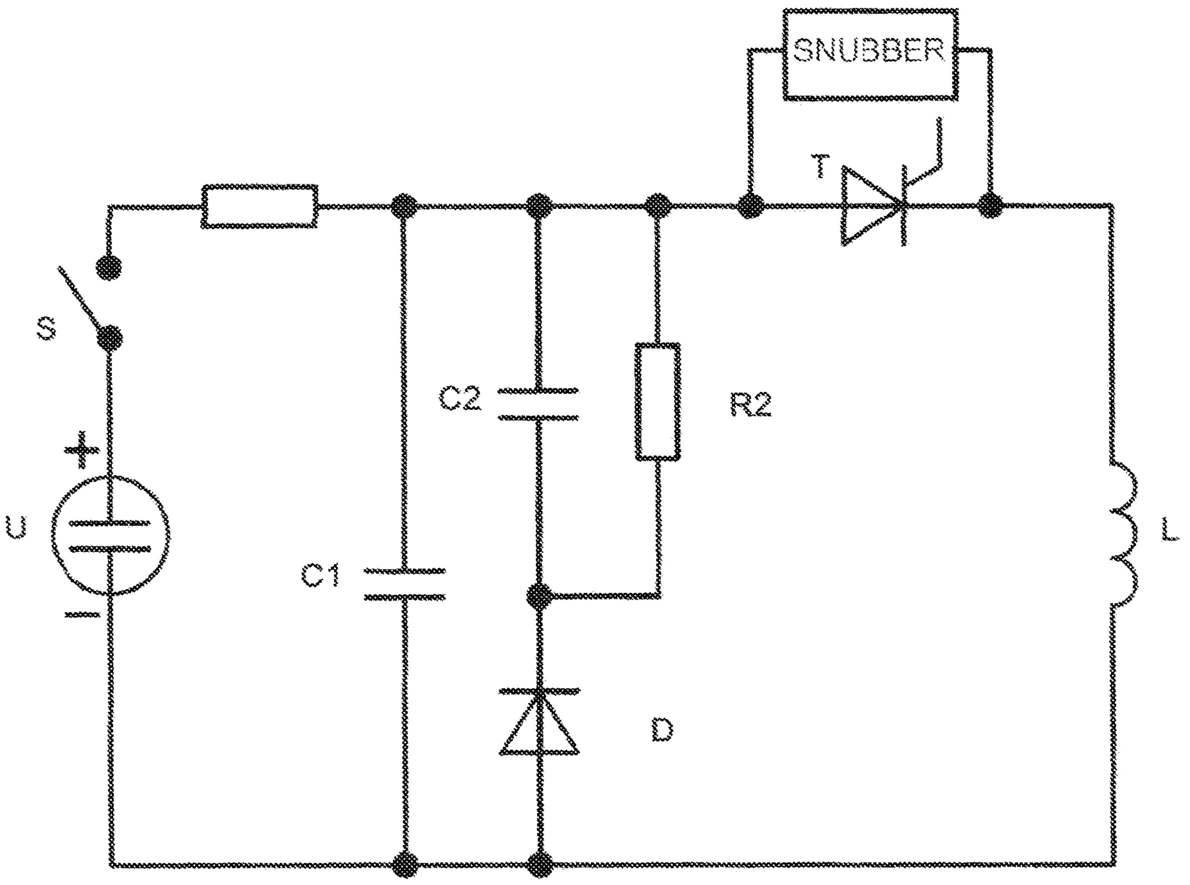
FIG. 6 represents the fifth embodiment of the circuitry of the monophasic magnetic stimulator for transcranial magnetic stimulation according to the invention.

FIG. 2 to 6 show examples of particularly advantageous embodiments of the arrangements of the monophasic magnetic stimulator according to the invention, while FIG. 2 represents the first variant of the implementation, containing in the branch with the diode D a series combination of the braking resistor R3 and the braking capacitor C2, to which the discharging resistor R2 is connected in parallel. In FIG. 2, a snubber is also connected in parallel to the thyristor T to protect it against the voltage peak that occurs when it is turning off. In FIG. 3, the connection is basically identical to FIG. 2, but it does not include the snubber, only illustrating a principle of the function not using the auxiliary circuits. FIG. 4 shows another possible arrangement of a monophasic magnetic stimulator, which is similar to the arrangement in FIG. 2. However, in the arrangement of FIG. 4, the discharging resistor R2 is connected in series. FIG. 5 and FIG. 6 then represent a substitute diagram of a monophasic magnetic stimulator arrangement according to another possible example of an arrangement in which the value of the braking resistor is essentially 0 ohms.

Examples of the values of the individual components according to one implementation of the arrangement of the monophasic magnetic stimulator according to the invention are as follows: the stimulation coil L is a coil with an inductance of 20 μH, which is of a type essentially identical to the coils used for magnetic stimulation in state-of-the-art stimulators or at least very similar to them, a stimulation capacitor C1 has a capacity of 200 μF and is designed for a voltage of at least 2.7 kV, the braking capacitor C2 has a capacity of 1200 μF and is designed for a voltage of 600 V, the braking resistor R1 has a value of 40 mΩ and the discharging resistor R2 has a value of 470Ω.

Figure 7:
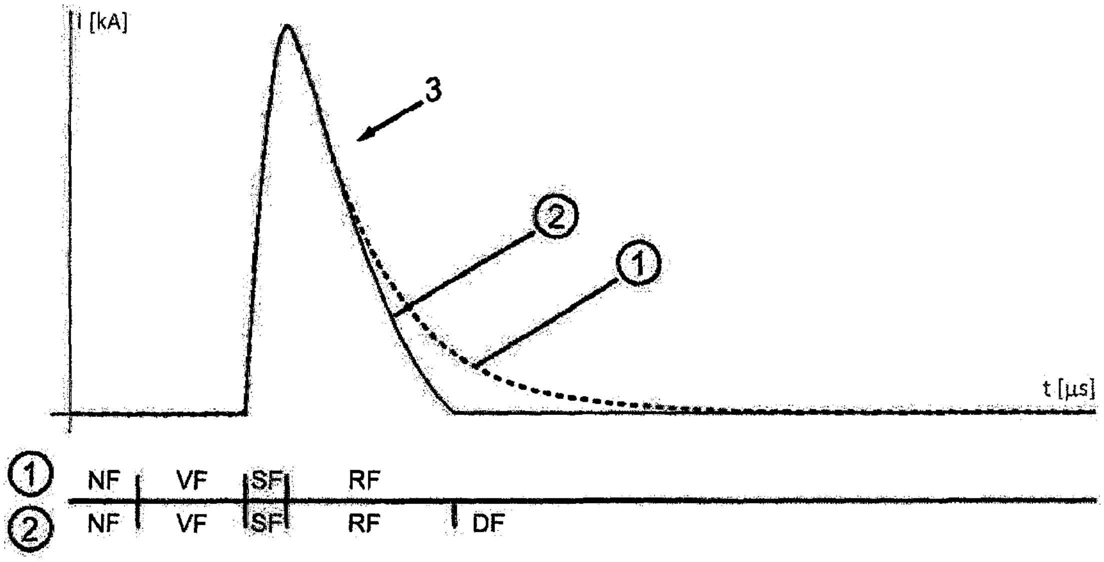
FIG. 7 represents a comparison of the course of the stimulation current of a monophasic magnetic stimulator according to the state of the art and according to the invention.
Figure 8:
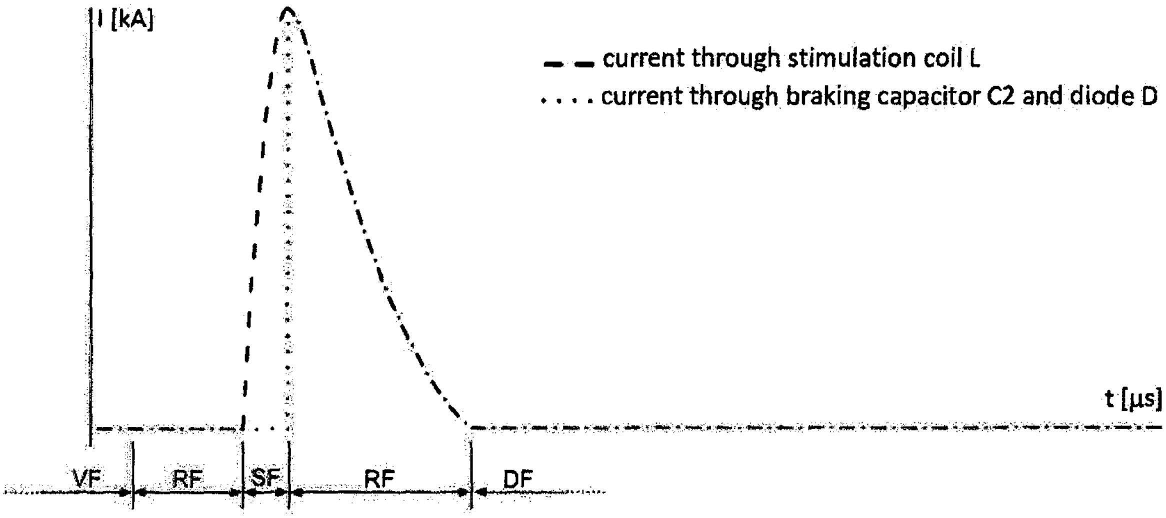
FIG. 8 represents the current waveforms through the stimulation coil and the branch with the braking capacitor and the diode of the monophasic magnetic stimulator according to the invention.

FIG. 7 represents a comparison of the course of the stimulation current of the monophasic magnetic stimulator according to the state of the art, which is shown by the dashed line, marked in FIG. 7 with reference number 1, with the course of the stimulation current of the monophasic magnetic stimulator for transcranial magnetic stimulation according to the invention. This course is shown in FIG. 7 by a continuous line, being marked with reference number 2. The following phases of the monophasic magnetic stimulator are marked on the timeline: charging phase CF, waiting phase WF, stimulation phase SF, relaxation phase RF and run-down phase DF. As is clear from the stimulation current waveforms, with a monophasic magnetic stimulator according to the state of the art, the relaxation phase is not completed and essentially merges with the run-up phase DF. Furthermore, FIG. 8 shows the course of the currents through the stimulation coil L and the circuit branch with the braking capacitor C2 and the diode D, in the embodiment of the monophasic magnetic stimulator in the embodiment according to FIGS. 5 and 6, respectively through a branch of the circuit with braking capacitor C2, braking resistor R1 and diode D, in case of the monophasic magnetic stimulator in the design according to FIGS. 2 to 4. On the timeline, in FIGS. 8 to 10, the individual phases of the magnetic stimulation pulse are marked in the same way as in FIG. 7, i.e. charging phase CF, waiting phase WF, stimulation phase SF, relaxation phase RF and run-down phase DF. Voltage curves and time periods are shown in FIG. 7 to 10 only for illustrative purposes, and their ratios may not correspond to the real values.

The operation of the monophasic magnetic stimulator according to the invention during the stimulation pulse is as follows:

a) Charging phase CF: this phase is identical to the charging phase of a monophasic magnetic stimulator according to the state of the art. The switch S is closed, the thyristor T is in the off-state because it is not energized. The stimulation capacitor C1 is charged to the voltage of the high-voltage source, on the order of 1 kV to 4 kV.

b) Waiting phase WF: this phase is again the same as the waiting phase of a monophasic magnetic stimulator according to the state of the art. Switch S is open and waiting for a stimulation impulse, while thyristor T is still in the off-state. Since the stimulation capacitor C1 discharges very slowly during this phase, in a particularly advantageous embodiment of the monophasic magnetic stimulator, its charging to the required voltage value is restored, for example by occasionally connecting the main source or by means of an auxiliary high-voltage source with low current. Since the diode D is polarized in the closing direction in the connection according to the invention in this phase, it does not participate in any energy exchange, including, of course, all the elements that are connected in series with it, that is, including the braking resistor R1, the braking capacitor C2 and the discharging resistor R2.

c) Stimulation phase SF: even the course of this phase is still the same as the course of the stimulation phase according to the state of the art in the case of the monophasic magnetic stimulator according to the invention. The stimulation phase is started by turning on the thyristor T using an external driver (not shown to simplify the connection). The thyristor T then remains in the on-state for the entire time during which a current which exceeds the holding limit passes through it. The holding limit of said current is usually about 1 A or lower. In the connection of the monophasic magnetic stimulator according to the invention, a standard type of thyristor meeting the required parameters is preferably used. On the contrary, IGCT thyristors with the possibility of switch-on commutation ( ) are not suitable, nor are terminally permeable thyristors or thyristors of a similar type.

The stimulation phase essentially corresponds to one quarter-wave oscillation of the LC circuit formed by the stimulation capacitor C1 and the stimulation coil L with a relatively high quality factor Q>approx. 10. There is a gradual increase in the current in the stimulation coil and a decrease in the voltage on the stimulation capacitor C1 until it is completely discharged. At this moment, the current flowing through the stimulation coil L has its maximum value, the energy of the electric field of the stimulation capacitor C1, being reduced by the losses mainly on the series resistance of the stimulation coil L, has been transferred into an energy of the magnetic field of the stimulation coil L to create the desired magnetic stimulation pulse. This completes the stimulation phase and, due to the inertia of the current in the stimulation coil L, there is a transition to the relaxation phase.

d) Relaxation phase RF: With the monophasic magnetic stimulator according to the invention, the relaxation phase has a similar course to the course of the relaxation phase of the monophasic magnetic stimulator according to the state of the art, until it reaches point 3 in FIG. 7, but then in the connection of the monophasic magnetic stimulator according to the invention, a reverse charging of the braking capacitor C2 and the stimulating capacitor C1 gradually occurs, the braking capacitor C2 having a decisive influence on the behavior of the RIC circuit due to its higher capacity. When the voltage on the diode D and the thyristor T is reversed, the diode D and the thyristor T turn off and the stimulation ends. The properties of this RLC circuit can be described as slightly damped having a quality factor Q>1. This qualitative change in the behavior of the circuit compared to the magnetic stimulator according to the state of the art occurred due to the inclusion of the braking capacitor C2 in series with braking resistor R1. Please note that the magnetic stimulator according to the state of the art have in the relaxation phase RF the quality factor Q less than 1. Due to the inclusion of the braking capacitor C2 in series with braking resistor R1, the circuit characteristic of the RLC circuit formed by R1, L and C1 and C2 changes due to the prevailing capacity of the braking capacitor C2, which is significantly larger than the capacity of the stimulating capacitor C1, it practically changes to the behavior of the RLC circuit formed by the braking resistor R1, the stimulating coil L and the braking capacitor C2, for which Q>1 already applies, therefore the exponential discharge of the 1st order changes to a discharge in the form of damped oscillations, which have regular passages with a zero current value. However, during the first such pass, the thyristor will turn off due to its behavior, as described above, and therefore no further oscillations will occur and the stimulation will end.

When comparing the monophasic magnetic stimulator according to the invention with the monophasic magnetic stimulator according to the state of the art, it can be seen that in the case of the magnetic stimulator according to the state of the art, during the relaxation phase, due to the inertia of the current in the stimulation coil 1, the voltage on the capacitor C1 further drops to negative values, which the diode D turns on, due to which the LC circuit, formed by the stimulation coil L and the stimulation capacitor C1, with a very high quality factor (Q>approx. 10) turns into a very damped RLC circuit with a very low quality factor Q<<1. Practically, the behavior of this circuit corresponds only to a RL circuit, which would mean that the current in the stimulation coil would decrease exponentially to zero with a time constant $\tau$=L/R1. This phase lasts for a very long time with the magnetic stimulator according to the state of the art, practically until the thyristor current drops below the holding current limit, which can be up to 14 time constants $\tau$, which is about 7 ms.

Figure 9:
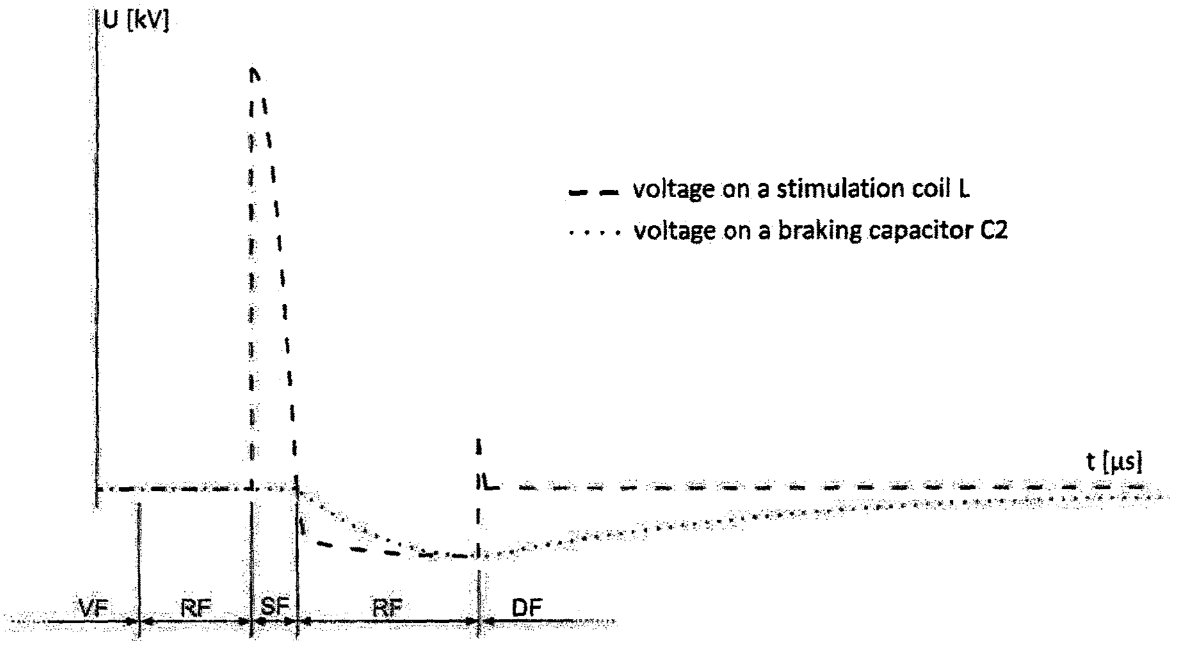
FIG. 9 represents the voltage curve on the stimulation coil and the braking capacitor of the monophasic magnetic stimulator according to the invention and FIG. 10 represents the voltage curve on the thyristor and the diode of the monophasic magnetic stimulator according to the invention.

As clear from the voltage curves in FIG. 9, after the start of the RF relaxation phase, the braking capacitor C2 is gradually charged, and in the region of the point 3 in FIG. 7, the influence of the braking capacitor C2 overbalances the influence of the braking resistor R1, so that the curve of the stimulation of the current in the magnetic stimulator according to the invention begins to differ significantly from the course of the stimulation current in the monophasic magnetic stimulator according to the state of the art. In the case of the monophasic magnetic stimulator according to the invention, the relaxation phase initially has a similar course to the course of the relaxation phase of the monophasic magnetic stimulator according to the current state of the art. There is an advantage that the stimulation parameters of the monophasic magnetic stimulator according to the invention are for the time when their intensity has a relevant influence on stimulation identical to the stimulation parameters of monophasic magnetic stimulators according to the state of the art. Thus the monophasic magnetic stimulator according to the invention exhibits at this time the same properties as the monophasic magnetic stimulator according to the state of the art, see the point 3 in FIG. 7. Due to this fact the monophasic magnetic stimulator according to the invention exhibits during the stimulation phase as well as in the mentioned first part of the relaxation phase the identical stimulation parameters as the monophasic magnetic stimulators according to the state of the art. Thus they differ only in the second part of the relaxation phase, when, on the contrary, there was a negative effect of the monophasic magnetic stimulators according to the state of the art. Thanks to said properties the monophasic magnetic stimulator according to the invention are fully usable instead of the monophasic magnetic stimulator according to the state of art. In particular, in the case of a connection in which the parallel combination of the resistances of the braking resistor R1 and the discharging resistor R2 has the same resistance value as the resistance of the braking resistor R1 in the case of a monophasic magnetic stimulator according to the state of the art, this course is particularly preferably substantially identical at its beginning.

e) Run-down phase DF: In this phase, the thyristor T is in the off-state and through the resistors R1 and R2, the voltage on the capacitor C2 is discharged to zero values with a time constant of several hundreds of microseconds to tens of milliseconds. A longer interval may be beneficial to reduce the penetration of the voltage drop across capacitors C1 and C2 through the snubber, if used in the circuit, into the stimulation coil, which may cause a small disturbance just after the end of stimulation. However, the vast majority of the discharging current takes place inside the magnetic stimulator, and theoretically no current passes through the stimulator coil. In practice, there are very weak thyristor and snubber leakage currents (on the order of tens of mA), but due to their small value, they do not cause interference in the sensed signal.

Figure 10:
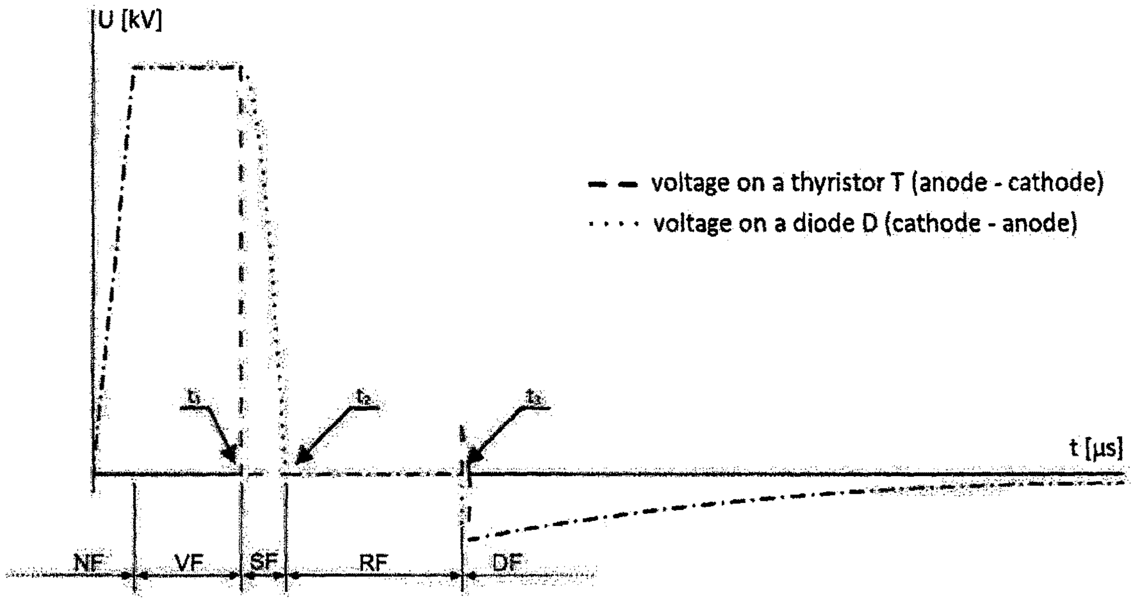

In FIG. 8, the course of the current through the stimulation coil L is indicated by a dashed line, and the course of the current of the branches with the braking capacitor C2 and with the diode D, respectively and braking resistor R1, marked with a dotted line. Sections in which the current courses are the same are marked with a dash-dotted line. In FIG. 9, the voltage curve on the stimulation coil L is marked with a dashed line, and the voltage curve on the braking capacitor C2 is marked with a dotted line. Sections in which the voltage waveforms are identical are marked with a dash-dotted line. As clear from FIG. 9, at the moment of turning off the thyristor T at the end of the relaxation phase RF, a voltage peak will be generated which could damage this thyristor, and therefore a snubber is advantageously used, which will be described later. FIG. 10 shows the course of the voltage on thyristor T and diode D during the stimulation pulse. At time t1, the thyristor T is turned on and stimulation begins, at time t2 the turning the diode D on ends the stimulation phase and begins the relaxation phase. At the moment t3, the stimulation pulse is terminated by turning the diode D and the thyristor T off.

The description of the function of the snubber in the monophasic magnetic stimulator according to the invention is as follows. In the application, the term “snubber” is understood as a device used to suppress voltage transient peaks in electrical systems. The connection of the monophasic magnetic stimulator in its particularly advantageous implementation contains a snubber, which has the task of reducing the pulse overvoltage that would otherwise appear when the thyristor T turns off at the end of the relaxation phase. When the thyristor is turning off, a voltage peak will occur, which could damage the thyristor due to exceeding its breakdown voltage. The snubber can be formed, for example, by a diode not shown here in series with a resistor not shown here, to which a second resistor not shown here is connected in parallel, but it can also be any other combination of components, ensuring protection of the thyristor against such a voltage peak. The parameters of the snubber have only a negligible effect on the parameters of stimulation and interference of the sensed signal and are therefore not the subject of this invention.

The snubber does not affect the stimulation parameters, the monophasic magnetic stimulator would provide the same function even without the use of a snubber. The purpose of the snubber is to reduce the voltage peak when the thyristor T is turning off. If the snubber was not used in the monophasic magnetic stimulator according to the invention, the technical solution would require the use of a thyristor T sized for substantially higher voltage, or it would be necessary to choose to connect more thyristors in series to increase the breakdown voltage in order to maintain the highest total allowable voltage on the thyristor. At a low value of the braking resistance R1, approaching its short circuit, i.e. approaching the value of 0 ohm, the magnetic stimulator would behave more "monophasically" because the size of the load impedance of the stimulation coil in the relaxation phase would be lower, the quality factor Q of the circuit L C2 higher, the course but the stimulation current, while still participating in the stimulation, would differ from the monophasic magnetic stimulators according to the current state of the art and this may not be accepted as a clinically equivalent method of stimulation. Therefore, the value of the resistance of the braking resistor R1 basically has no significant effect on the quality and speed of stabilization of the stimulation current during response registration, so it can also have a value close to 0 ohm.

The discharging resistor R2 has the task of discharging the braking capacitor C2 to zero voltage, so that the braking capacitor C2 is able to receive another charge under the same conditions as if it was the first stimulation, and therefore all the waveforms of the current of the stimulation pulses can be the same.

With the arrangement of a monophasic magnetic stimulator according to the current state of the art, the presence of a snubber is not necessary, as the thyristor will turn off only when the current drops below its holding current, which is very low (less than approx. 1 A). In contrast to that, the monophasic magnetic stimulator according to the invention has the magnitude of the current flowing through the thyristor when it is turning off of the order of kA.

The invention claimed is:

1. A circuit wiring arrangement of a monophasic stimulator for transcranial magnetic stimulation, comprising:
- a stimulation capacitor (C1) connected via a switch(S) and a limiting means (Rp) to a source (U) of a stimulation energy,
- a stimulation coil (L1) connected in parallel to the stimulation capacitor (C1) via a switching thyristor (T), wherein
- a braking capacitor (C2) connected in series with a diode (D), the braking capacitor (C2) and the diode (D) connected in parallel to the stimulation capacitor (C1), the braking capacitor (C2) arranged to speed up the closing of the diode (D), and
- a discharging resistor (R2) connected in parallel to the braking capacitor (C2), the braking capacitor (C2) having an electrical capacity at least equal to or greater than the electrical capacity of the stimulating capacitor (C1).

2. The circuit wiring arrangement of the monophasic stimulator for transcranial magnetic stimulation according to claim 1, wherein the braking capacitor (C2) has an electrical capacity at least four times bigger than the electrical capacity of the stimulating capacitor (C1).

3. The circuit wiring arrangement of the monophasic stimulator for transcranial magnetic stimulation according to claim 1, wherein a braking resistor (R1) is connected in series between the diode (D) and the brake capacitor (C2), wherein the discharging resistor (R2) is connected in parallel to both the braking resistor (R1) and the brake capacitor (C2).

4. The circuit wiring arrangement of the monophasic stimulator for transcranial magnetic stimulation according to claim 1, wherein a snubber (S) is connected in parallel to the switching thyristor (T).

5. The circuit wiring arrangement of the monophasic stimulator for transcranial magnetic stimulation according to claim 1, wherein the braking capacitor (C2) has a braking capacitor (C2) electrical capacity in the range of four times to ten times the electrical capacity of the stimulation capacitor (C1).

6. The circuit wiring arrangement of the monophasic stimulator for transcranial magnetic stimulation according to claim 1, wherein a braking resistor (R1) is connected in series between the diode (D) and the brake capacitor (C2), wherein the discharging resistor (R2) is connected in parallel only to the brake capacitor (C2).

* * * * *